(12) United States Patent  
McCabe et al.

(10) Patent No.: US 6,521,320 B2
(45) Date of Patent: Feb. 18, 2003

(54) PANTS TYPE DIAPER AND METHOD FOR PRODUCTING SAME

(75) Inventors: John A. McCabe, Sheboygan Falls, WI (US); Richard J. Nehrlich, Elkhart Lake, WI (US); Bradley M. Dahmer, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 10/085,908

(22) Filed: Feb. 28, 2002

(65) Prior Publication Data

US 2002/0092604 A1 Jul. 18, 2002

Related U.S. Application Data

(62) Division of application No. 09/537,157, filed on Mar. 29, 2000.

(51) Int. Cl.$^7$ ................................. A61F 13/15
(52) U.S. Cl. .................. 428/137; 428/200; 604/385.27
(58) Field of Search ......................... 428/131, 137, 428/200; 604/385.24, 385.25, 385.26, 385.27

(56) References Cited

U.S. PATENT DOCUMENTS

| 5,147,487 A | 9/1992 | Nomura et al. |
| 5,188,627 A | 2/1993 | Igaue et al. |
| 5,213,645 A | 5/1993 | Nomura et al. |
| 5,634,917 A | 6/1997 | Fujioka et al. |
| 5,643,396 A | 7/1997 | Rajala et al. |
| 5,645,543 A | 7/1997 | Nomura et al. |
| 5,660,657 A | 8/1997 | Rajala et al. |
| RE35,687 E | 12/1997 | Igaue et al. |
| 5,745,922 A | 5/1998 | Rajala et al. |
| 5,749,989 A | 5/1998 | Linman et al. ............. 156/160 |
| 5,836,931 A | 11/1998 | Toyoda et al. |
| 5,879,500 A | 3/1999 | Herrin et al. |
| 6,315,022 B1 | 11/2001 | Herrin et al. ............... 156/459 |
| 6,375,769 B1 * | 4/2002 | Quereshi et al. ........... 156/73.1 |

* cited by examiner

Primary Examiner—James Sells
(74) Attorney, Agent, or Firm—Ryan Kromholz & Manion, S.C.

(57) ABSTRACT

A pants-type diaper, is provided which is equipped with leg-hole elastics which effectively encircle the leg-holes without traversing the crotch region. Also provided are methods for producing such diapers. Typical products of this type are provided with an outer laminate, formed of an inner liner material and an outer backsheet material between which the leg-hole elastics are disposed. The invention provides for the removal of a strip of inner liner material carrying undesirable crotch-region elastic strands prior to lamination or combining of the remaining inner liner with a complementary outer layer backsheet.

8 Claims, 19 Drawing Sheets

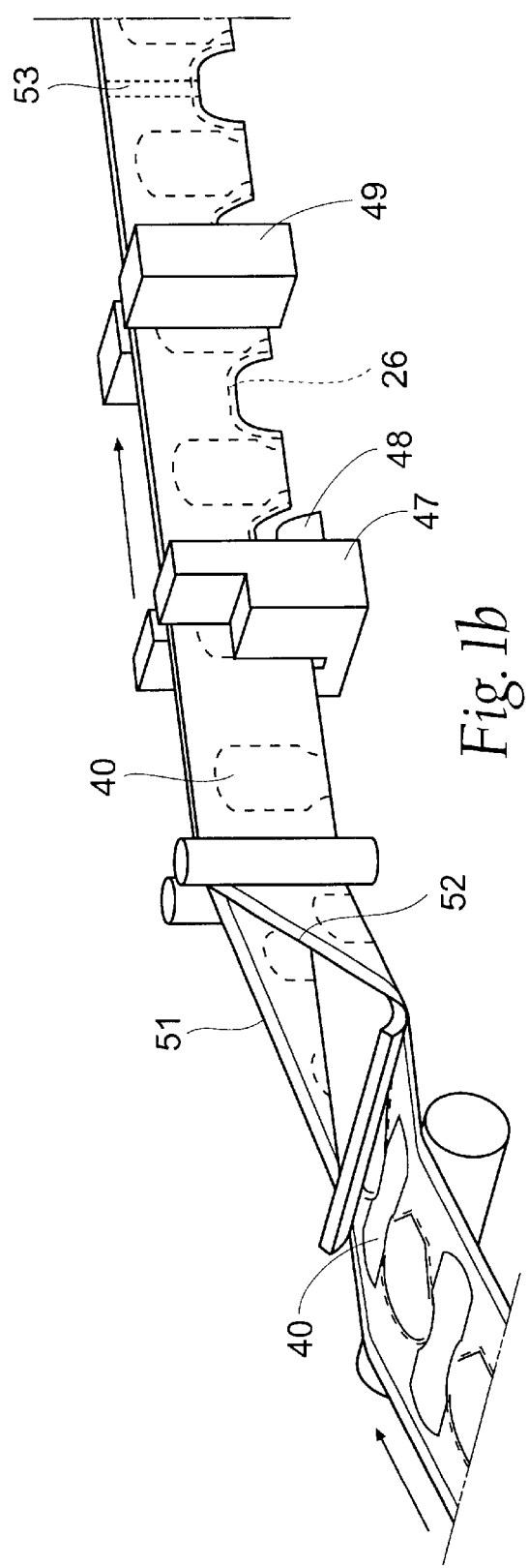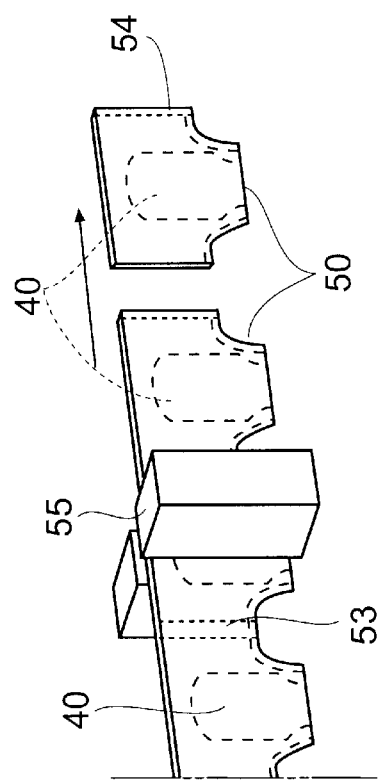

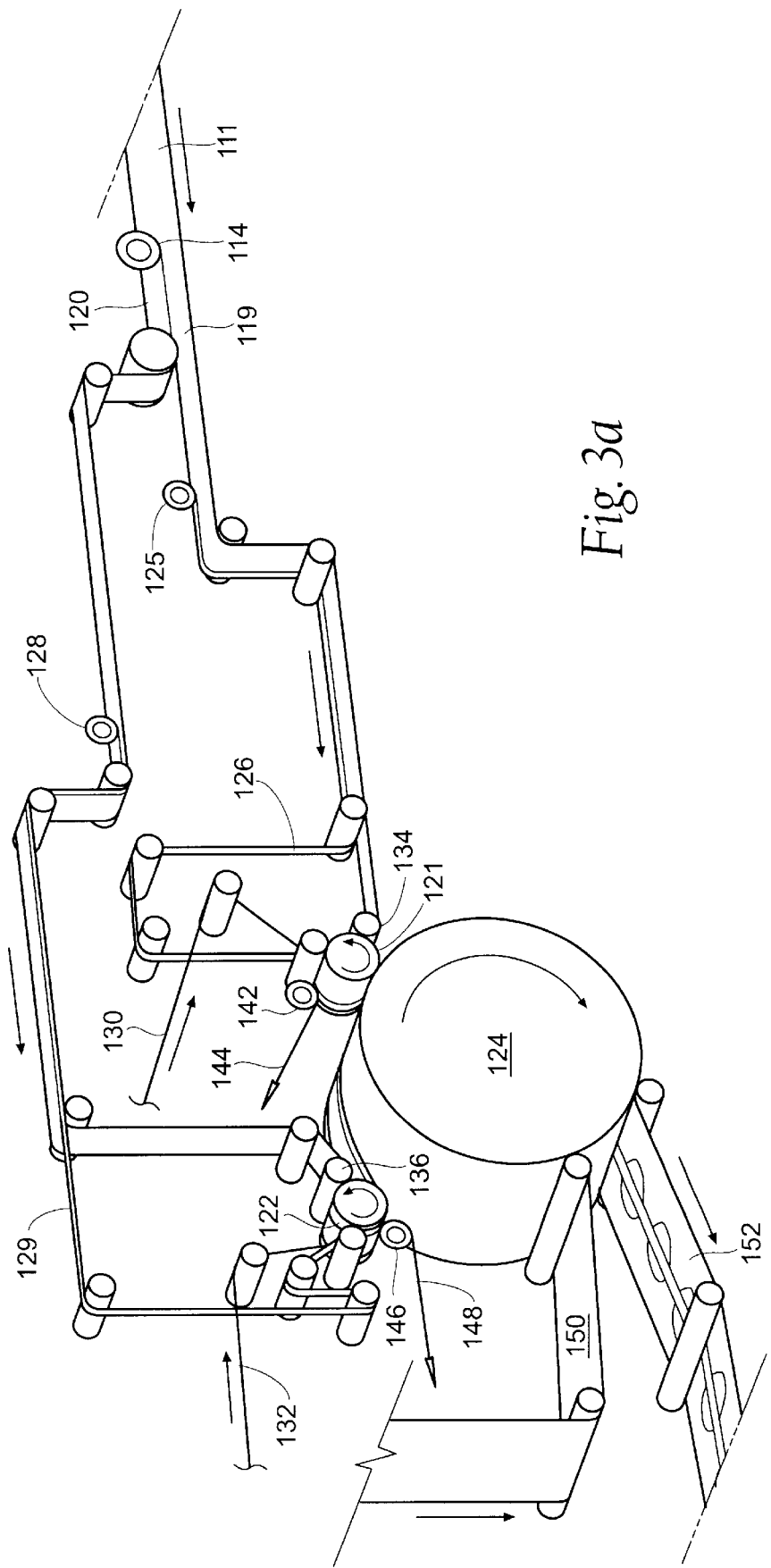

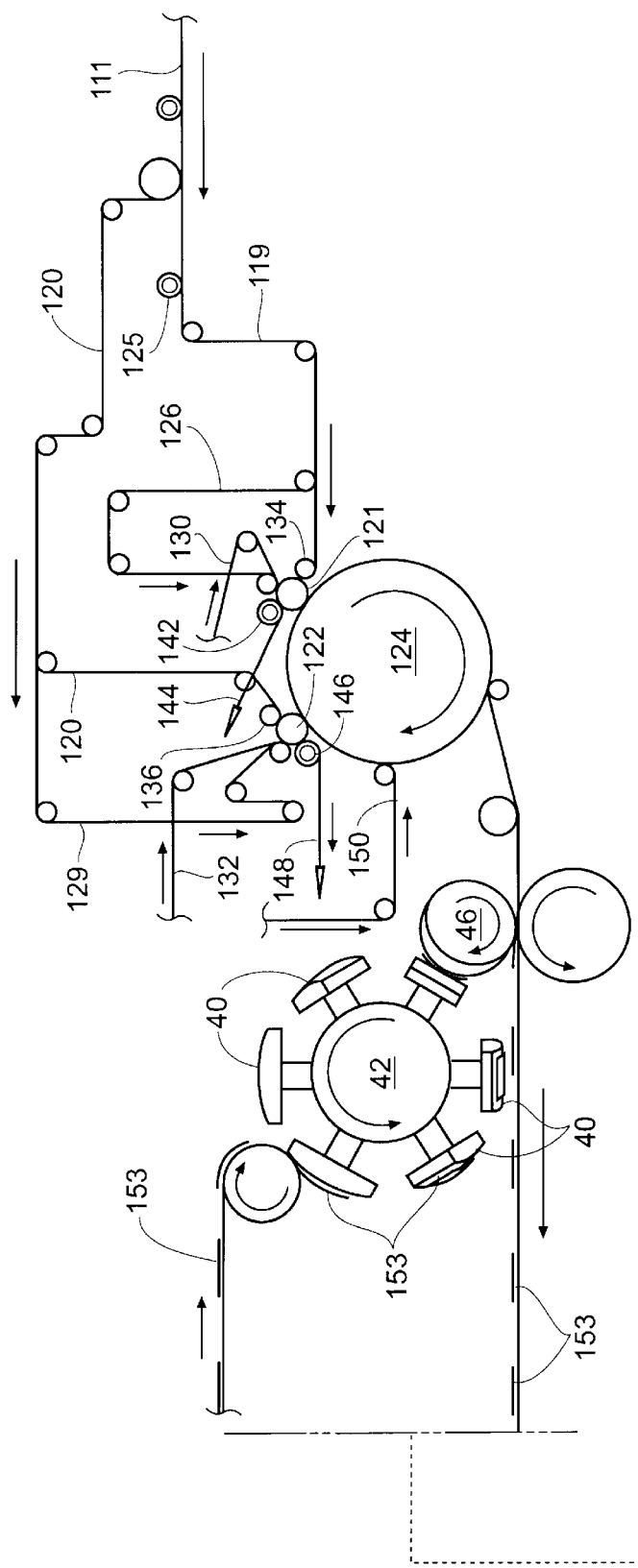
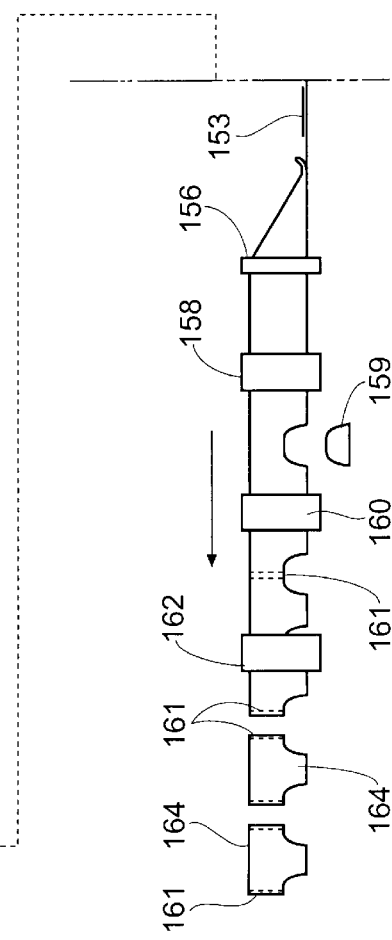
Fig. 4

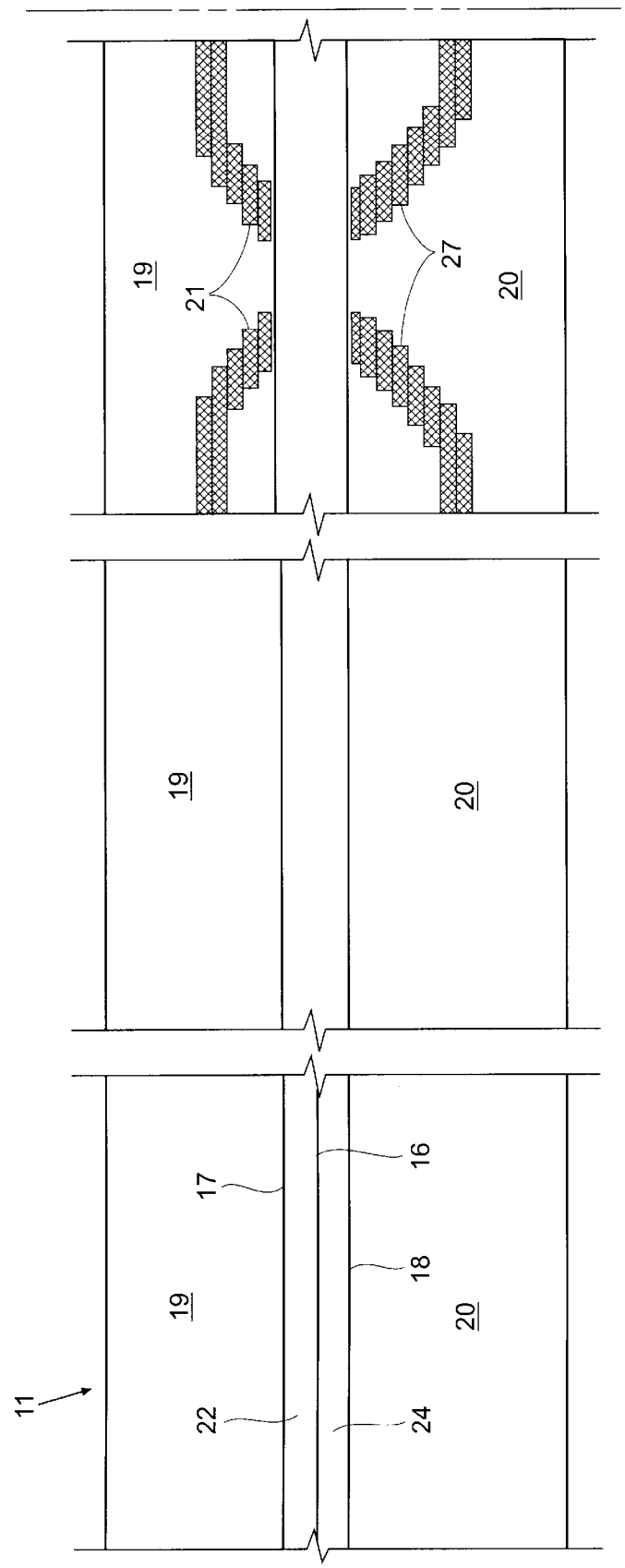

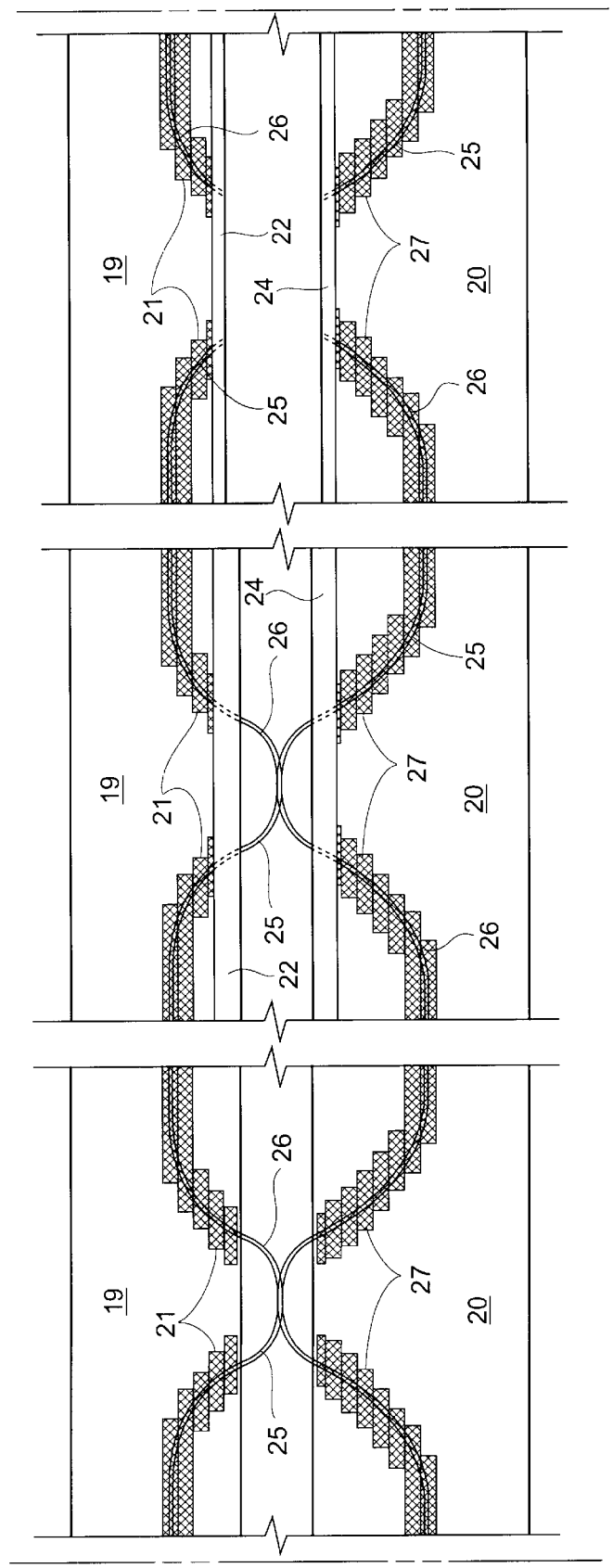

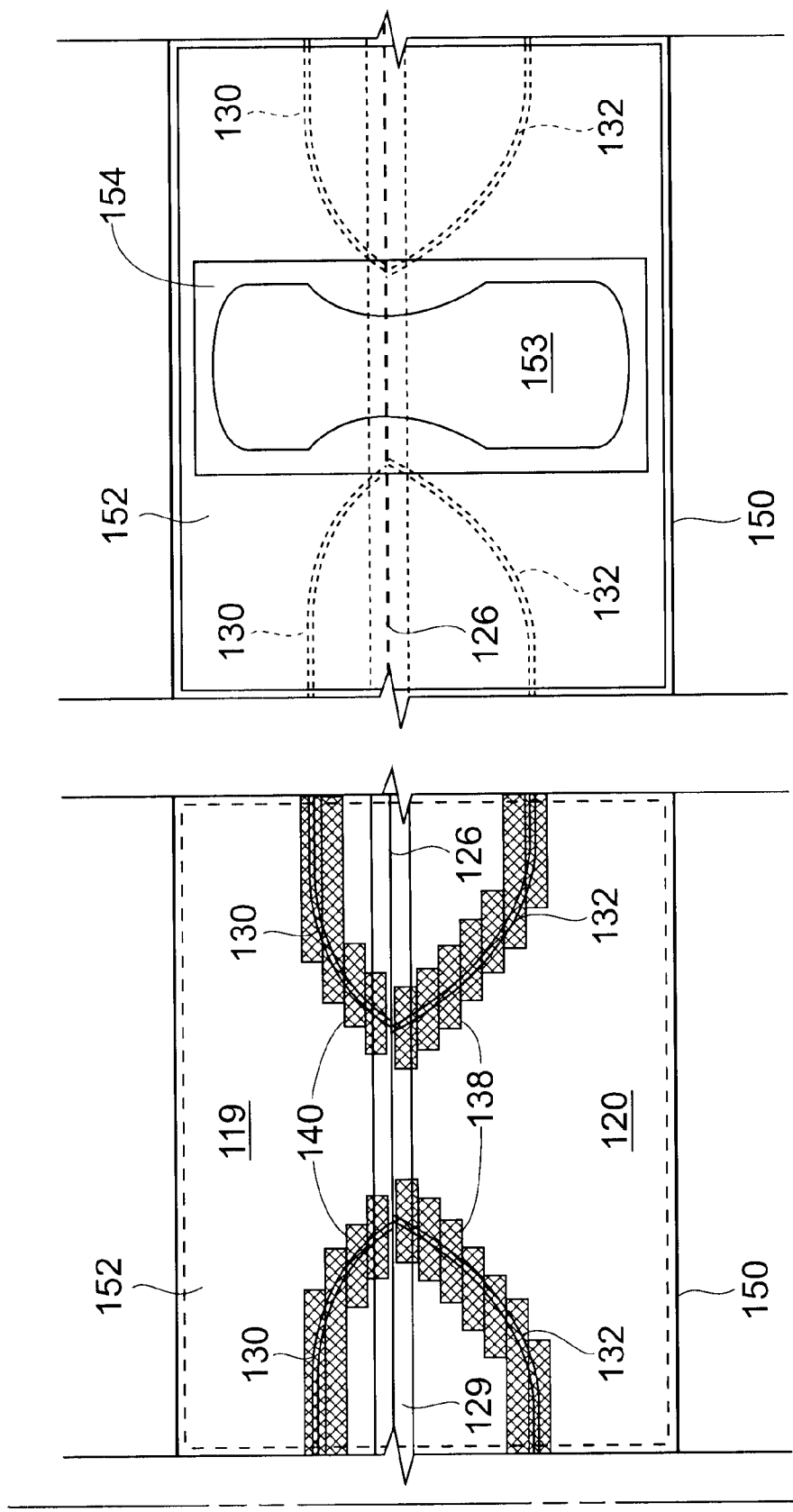

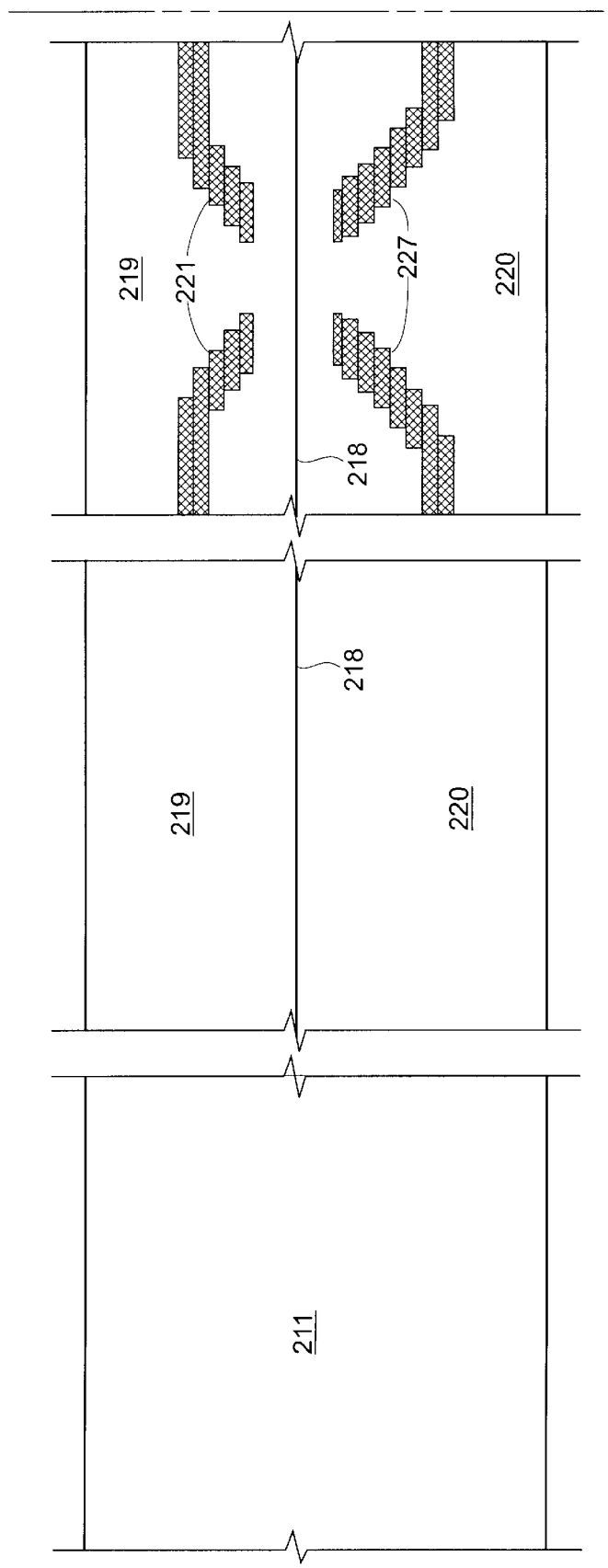

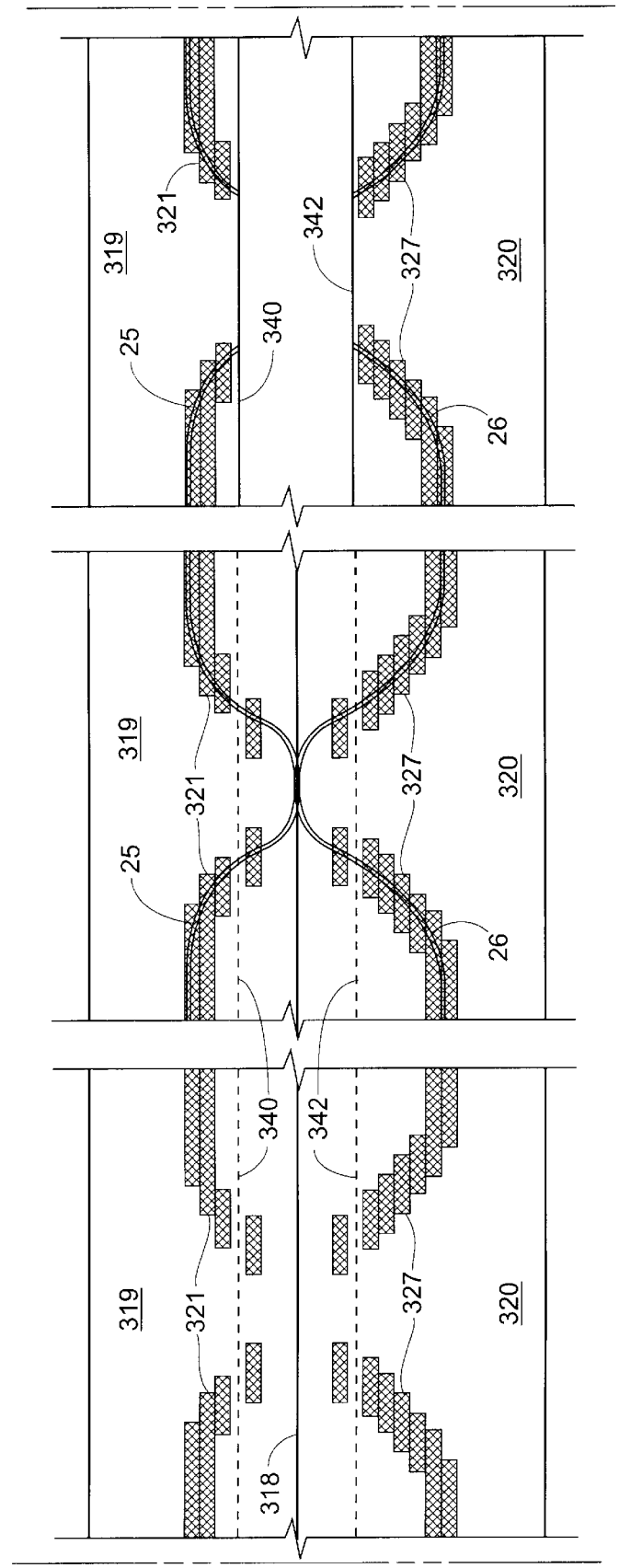

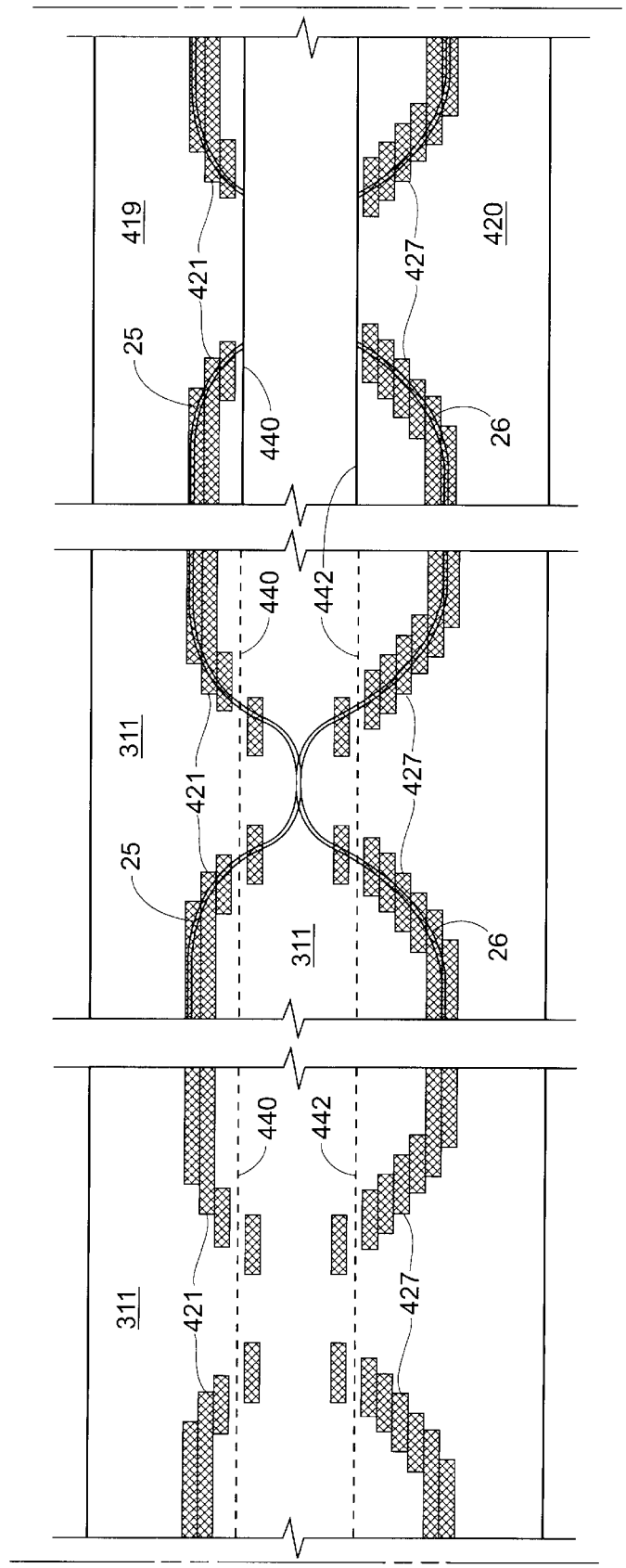

PANTS TYPE DIAPER AND METHOD FOR PRODUCTING SAME

RELATED APPLICATION

This is a divisional application of application U.S. Ser. No. 09/537,157, filed Mar. 29, 2000.

BACKGROUND OF THE INVENTION

The invention relates to disposable garments, and more particularly, a pants-type diaper, which is equipped with elastics strips effectively encircling the leg-holes without traversing the crotch region and to a method for producing such diapers.

Disposable diapers of the children's training pant type, or of the adult incontinence type, are typically equipped with elastic strands, which encircle the leg-holes. These strands of elastic are typically captured with adhesive between two layers of nonwoven materials. Various methods are used to position these elastic strands so that they produce the desired encircling effect.

In one method of manufacture, the diapers are produced in an orientation whereby product flow is in the form of a single continuous web and the direction of travel is at a right angle with respect to what would be described as the crotch line of the diaper, i.e., the normal direction of product flow is parallel to the waist as opposed to parallel to the crotch.

One method of creating the desired effect of encircling the leg holes of the pant with elastics is to interleave two swaths of elastic strands, each curving across the face of the traveling web, encircling about one half of the leg-hole areas and crossing the path of the other. As a pair, they create a boundary around each leg-hole cutout, which resembles a circle or ellipse. In practice, however, the lateral excursions of the elastic lay-down device are speed-limited. As the traveling web is moving at some speed in one direction, and as the elastic lay-down device has speed and acceleration limits in the cross-direction, there is a limit to the steepness of the oblique angle which it is possible to form between the two. The result of this limitation is usually seen in the form of apparent incompleteness in the formation of the leg-hole-encircling pattern, particularly at the crotch line, where the two swaths cross each other.

From the point on the web at which one leg-hole pattern has been completed to the point at which the next can be begun, the elastic laydown device must reposition itself to a favorable starting point. This period of repositioning occurs as the crotch region passes the laydown device. As a result, the elastic strands must also cross this region of the product, at which they may or may not be attached by means of adhesives to the carrier webs. Various means are used to control or limit the positional relationships of the elastic strands in this region. The two sets of strands may cross over each other, creating an "X" pattern, or, they may loop back over to their respective sides, creating an "O" at the center of the crotch region. Alternatively, they may be mechanically stopped and prevented from crossing each other, creating two sets of generally parallel lines at the crotch The lay-down pattern used at the crotch will determine the final appearance of the product in this area.

The shirring effect created by elastic strands when laminated with any flexible fabric is well known. However, to have this shirring effect applied to the crotch of a pant-type garment can be undesirable. The elastics create a contractile force, which tends to distort the garment at this location, thereby reducing the garment's aesthetic appeal, effectiveness and comfort. Thus various methods of reducing or eliminating the effects of the elastic tension normally occurring at the crotch have been attempted. These methods include the elimination of the adhesive bond between the strands and the liner materials described in U.S. Pat. No. 5,745,922 as "unsecured space" as well as various methods of cutting the strands to eliminate their effects.

While the presence of the leg-hole elastic strands at the crotch region is claimed by some to be of benefit in biasing the diaper's inner cuffs against the user's legs see U.S. Pat. No. 5,188,627; Igaue, et al, it is believed by the present applicants that the disadvantages, described above, outweigh any advantages.

As mentioned, one method of eliminating the undesired effects of the elastic strands which cross the crotch region is to sever them. This method is described in U.S. Pat. No. 5,660,657. Unfortunately, such severing usually requires the introduction of a transversely extending cut, which can result in a loss of web tension in the severed part of the carrier web. This also creates an undesirable opening in the diaper backsheet. A proposed solution for this problem is taught in U.S. Pat. No. 5,707,470, wherein an ultrasonic device is used to sever the elastic members, while the carrier webs which encapsulate the elastics are left intact. See, also, U.S. Pat. No. 5,643,396. Another problem associated with such severing lies in the tendency of the unsecured severed ends of elastic to retract to some point beyond the limits of any adhesive pattern. Thus, the elastic strands are not controlled or anchored near the ends of the adhesion pattern and may snap back to further into the adhesive pattern. This results in an incomplete elastic pattern and poor product characteristics.

One method of compensating for the incompleteness of the encircling pattern entails insertion of an additional set of elastic strips, running parallel to the crotch line and transverse to the web path. See U.S. Pat. Nos. 5,634,917 and 5,660,657. Typical products of this type are provided with an outer laminate, which is formed of an inner liner material and an outer backsheet material, between which the leg-hole elastics are disposed.

SUMMARY OF THE INVENTION

It is a principal object of this invention to provide an improved method of producing pants type diapers and to provide the resultant improved diapers. A pants-type diaper, is provided which is equipped with leg-hole elastics which effectively encircle the leg-holes without traversing the crotch region.

In accordance with one aspect of the invention, elastic strands are eliminated from the crotch region of a pants type diaper. In accordance with a related aspect, the invention provides a method wherein undesirable elastic material is encapsulated and then an interior longitudinal zone of material which contains the. undesirable elastic is cut away and removed. The invention provides for the removal of a strip of inner liner material carrying the undesirable crotch-region strands before the remaining inner liner is combined or laminated with its complementary outer backsheet layer.

In accordance with a further related aspect, the remaining webs, which contain elastic strands, are subsequently laminated with a cover sheet. In a preferred embodiment of the invention, the remaining webs may be rejoined before lamination, thereby reducing the segment of leg opening perimeter which is removed.

In one embodiment, the leg-hole elastic swaths are laid down on an inner non-woven carrier web, following appropriate curving patterns. The resultant composite web is then longitudinally slit into two narrower webs. The inside edge of each narrower web is then folded longitudinally to cover that part of the elastic pattern which is to be removed. This operation serves to cover the exposed adhesive and to entrap the elastics in this area. The entrapped elastics and the material within which they are enclosed are then removed by again slitting the edge of the webs and scrapping the waste edges. The remaining webs, with their semicircular elastic patterns intact may then be subsequently brought back to positions of contiguity by guiding means. This relocation brings the two semi-circles together to form more nearly perfect elastic circles or ellipses. The two narrower webs are then laminated with an outer carrier web, which entraps the remaining elastic swaths, creating a final laminated outer backsheet for the pant-type diaper. Subsequent processes insert an absorbent chassis or pad, cut out the leg-hole, fold the web longitudinally, and seal and cut the web into individual pants type diapers.

A second embodiment of the invention involves a similar process, but differs, in that instead of folding the slit edge of the web over to cover and entrap the elastics which are to be removed, separate strips of web material are introduced for this purpose. Such web strips may be obtained by slitting them from either the outer or inner edges of two narrow webs.

A third embodiment, a variant of the second embodiment, covers and entraps the elastics with a single, wider strip of material. Such web may be an edge previously cut and removed from the inner liner material or may be separate material provided for this purpose.

A fourth embodiment may be similar to one of the first, second or third embodiments, but differs in that the two narrow webs are not brought together prior to lamination. Instead, the gaps or missing segments between two semi-circles around the leg openings are replaced by elastics provided in the edges of an absorbent chassis or pad, which overlays the crotch area.

In a yet further embodiment of the invention the intermediate narrow strip of material is eliminated. A single web, or if desired, a pair of traveling webs are provided onto each of which an adhesive pattern is applied. The elastic strips are laid down on the adhesive in a serpentine pattern. The strips may be firmly secured to the adhesive by pressing them into the adhesive, for example, by using a pressure roll. A chilled slitting knife may be used in order to minimize adhesive build-up or contamination on the knives. Also, the adhesive can be applied in a pattern which leaves a gap in a strip along which slitting takes place, order to facilitate clean cutting of the composite web. After slitting and removal of the trim, a back sheet is applied which results in the elastic strips being sandwiched between the slit webs and the backsheet.

Briefly, a preferred method of the invention includes the steps of providing a web, defining on the web a portion of a pants type diaper including locations for leg openings and a crotch area there between. Then, a layer of adhesive is applied around the leg openings and across the crotch area.

An elastic ribbon is laid down on the adhesive in a semicircular pattern around the leg openings and across the crotch area. Subsequently a narrow web is laid down over the elastic and the adhesive in the crotch area. Then the web is longitudinally slit to sever at least a portion of the narrow web and the unwanted elastic in the crotch area. The removed materials are scrapped, resulting in a pants-type diaper without elastic in the crotch region.

A cover sheet is laminated over the remaining web, and, all material is removed from the leg openings. An absorbent pad is preferably attached over the crotch area. The absorbent pad may optionally be provided with elastic strips adjacent opposite lateral edges which serve to complete the encirclement of the leg openings by elastic material.

The invention, thus, produces a disposable garment including a front body portion, a back body portion and an intermediate crotch portion with spaced left and right leg openings on opposite sides of said crotch portion. The edges of the front and back body portions are joined to form a waist portion, the leg openings each having an upper periphery adjacent to the waist portion and a lower periphery adjacent to the crotch portion. The garment, further, includes a back sheet which forms an outer surface thereof, a top sheet and an absorbent pad positioned in the crotch area. In accordance with the invention, there are front left and right elastic strands which extend, respectively, around a quadrant of each of the leg openings from forward ends which terminate at a forward part of the crotch portion and around the upper periphery of each of the left and right leg openings to the side seam. Similarly, rear left and right elastic strands extend, respectively, around another quadrant of each of the leg openings from rearward ends which terminate at a rearward part of the crotch portion and extend around the upper periphery of each of the left and right leg openings to the side seam. The strands are adhered to the top sheet, and to first and second narrow webs sandwiched between the top sheet and the back sheet. The first narrow web is adhered to the forward ends of each of the left and right elastic strands and the second narrow web is adhered to the rearward ends of each of the left and right elastic strands.

In its most basic form, the invention provides a method of forming pants type diapers which includes the steps of (a) providing a traveling fabric web upon which is defined a portion of a pants type diaper including locations thereon for leg openings and a crotch area therebetween, (b) applying an adhesive pattern on the web around the leg openings, (c) laying down strips of elastic material on the adhesive in an undulating pattern around the leg opening locations on the traveling web and across the crotch area, (d) forming a pair of parallel longitudinal slits along the center of the traveling web to sever the central portion of the web thereby severing the elastic in the crotch area, (e) removing the severed portion of the traveling web and the elastic, laminating a cover sheet over the severed halves of the traveling web, (f) cutting and removing all material from the leg openings, (g) severing the web into individual diaper blanks, (h) folding the blanks in half across the crotch area, and, (i) sealing the edges of the blank together on each side thereof to form a pants-type diaper.

Further objects and advantages of the invention will be apparent from the following detailed description, the attached claims and the drawings.

BRIEF DESCRIPTION OF THE DRAWINGS

FIGS. 1a–1c, collectively, are a perspective view showing a preferred embodiment of the invention in somewhat diagrammatic fashion;

FIGS. 3a–3b are, collectively, a perspective view showing in somewhat diagrammatic fashion an alternative embodiment of the invention;

FIG. 4 is a diagrammatic view further illustrating the process and equipment shown in FIGS. 3a–3b;

FIGS. 5a–5g are a series of fragmentary plan views showing sections of the web as it passes through the process and apparatus of FIGS. 1a–1c and 2;

FIG. 5h is a fragmentary plan view showing a step subsequent to that depicted in FIG. 5g but viewed from the opposite side of the web;

FIG. 6a is a fragmentary plan view showing a web section at a point where it leaves combining role number 124 in FIG. 3a;

FIG. 6b is a fragmentary plan view viewed from the opposite direction shown in FIG. 6a and showing a section of the web after it leaves roller 46 depicted in FIG. 3b;

FIGS. 7a–7g are fragmentary top plan views showing yet another embodiment of the invention;

FIG. 7h is a fragmentary top plan view taken from the opposite of the web shown in FIGS. 7a–7g at a subsequent point in the process;

FIGS. 12a–12c are a series of fragmentary plan views showing sections of webs as passing through the process and apparatus of FIG. 11; and, FIGS. 13a–13c are another series of fragmentary plan views showing sections of webs as passing through the apparatus of FIG. 11 in accordance with a modified process.

DETAILED DESCRIPTION OF THE INVENTION

Figure 1A:
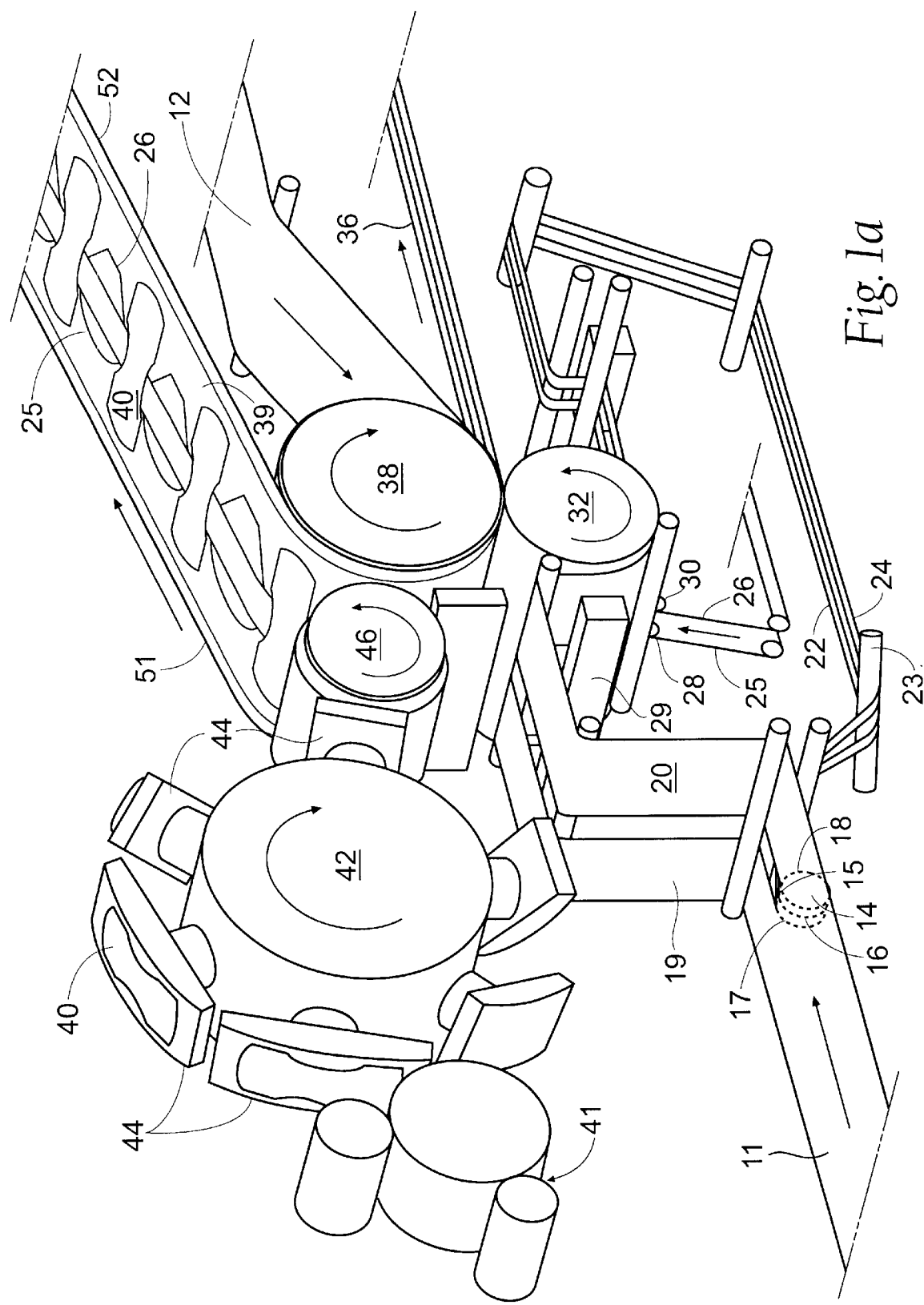

Referring first to FIGS. 1a, 1b and 1c, one of the preferred embodiments of the process of this invention and related apparatus are illustrated. The process utilizes two main carrier webs; a non-woven web 11 which forms an inner liner web, while web 12 forms an outwardly facing layer in the finished diaper. In this embodiment, non-woven web 11 is slit, at slitter station 15, by rotary knives 14 along three lines. One of these, line 16, is on approximately the centerline of web 11 and two additional lines 17 and 18 are parallel to and spaced a short distance from centerline 16. (See FIG. 5a.) The effect is twofold, first, to separate web 11 into two halves, as also seen in FIG. 5b. One half, 19, will become the inside of the front of the diaper 50 and the second half, 20, will become the inside of the back of that garment. Second, two separate, relatively narrow strips 22 and 24 are formed which are subsequently used to cover and entrap portions of the leg-hole elastics 25 and 26. Strips 22 and 24 are separated physically by an angularly disposed spreader roll 23 and aligned laterally with their downstream target positions on the inner edges of webs 19 and 20.

As shown in FIG. 5c, adhesive patterns 21 and 27 are applied to the web halves 19 and 20 in the target areas for the leg hole elastics 25 and 26. A spray gun assembly 29 of a type known in the art is preferably used to apply adhesive patterns 21 and 27. Two sets of leg-hole elastic strands 25 and 26 are introduced through laydown guides 28 and 30, which reciprocate from side to side past each other. Strands 25 and 26 are glued to the web sections 19 and 20, their laydown patterns following a serpentine path. Given the absence of adhesive in the area separating web 19 from web 20, for some portion of each successive diaper product, the strands 25 and 26 each track parallel to the inner slit edges of the web sections 19 and 20. Laydown guides 28 and 30, thus, apply the strands 25 and 26 which form leg-hole elastics as the web sections 19 and 20 are carried along the face of a drum or roll 32. Those parts of the elastic patterns which are near the inner slit edges of webs 19 and 20 are then covered by the introduction of an adhesive lamination thereover of the strips 22 and 24 of non-woven web also against the drum 32.

Figure 2:
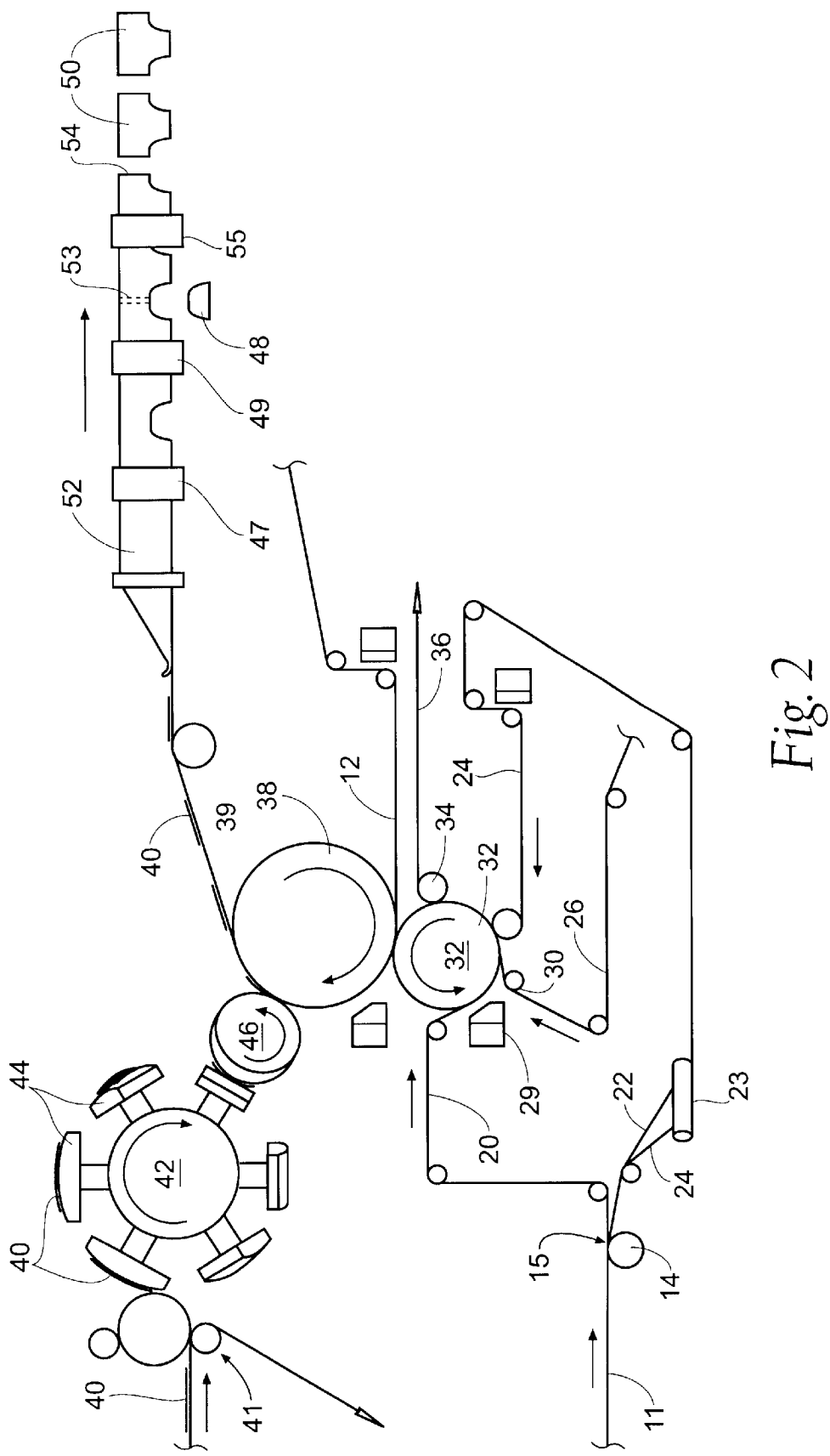
FIG. 2 is a diagrammatic view of the equipment and process shown in FIGS. 1a–1c.

The side-to-side excursions of the leg-hole elastic laydown guides 28 and 30 result in arcuate segments of elastic strands extending on each side of the web centerline as seen in FIGS. 5d and 5e. After the non-woven strips 22 and 24 have been applied to cover and entrap those parts of the elastics 25 and 26 which run nearest to and parallel to the inner edges of the webs 19 and 20, a second pair of slitter knives 34 (FIG. 2) are used to trim away a portion of the narrow non-woven strips 22, 24, along with that part of the inner liner webs 19, 20 to which they are laminated. This also removes those portions of the elastic strands 25, 26 which are contained within the laminations. The resultant trimmed scrap strips 36 are removed from the process for disposal elsewhere.

The effect of the last-described step is to totally remove the cut away portions of the elastic, eliminating its corresponding unwanted gathering effect from the crotch region of the garments 50. The remaining portions of the curved elastic strands create a gathering effect around the leg openings of the finished garments 50.

Subsequent to the combining and trimming of the inner webs 19, 20 and the cover strips 22, 24, the combining drum 32 carries the webs to a point of approximate tangency with a second combining drum 38, where the web sections 19, 20, with their respective curved elastic patterns 21 and 27 exposed, are transferred to and laminated adhesively against the inside face of outer liner web 12. This process entraps the curved elastic patterns 25, 26 between the inner and outer chassis webs 19, 20 and web 12 thereby forming a composite web 39.

Figures 5G, 5H:
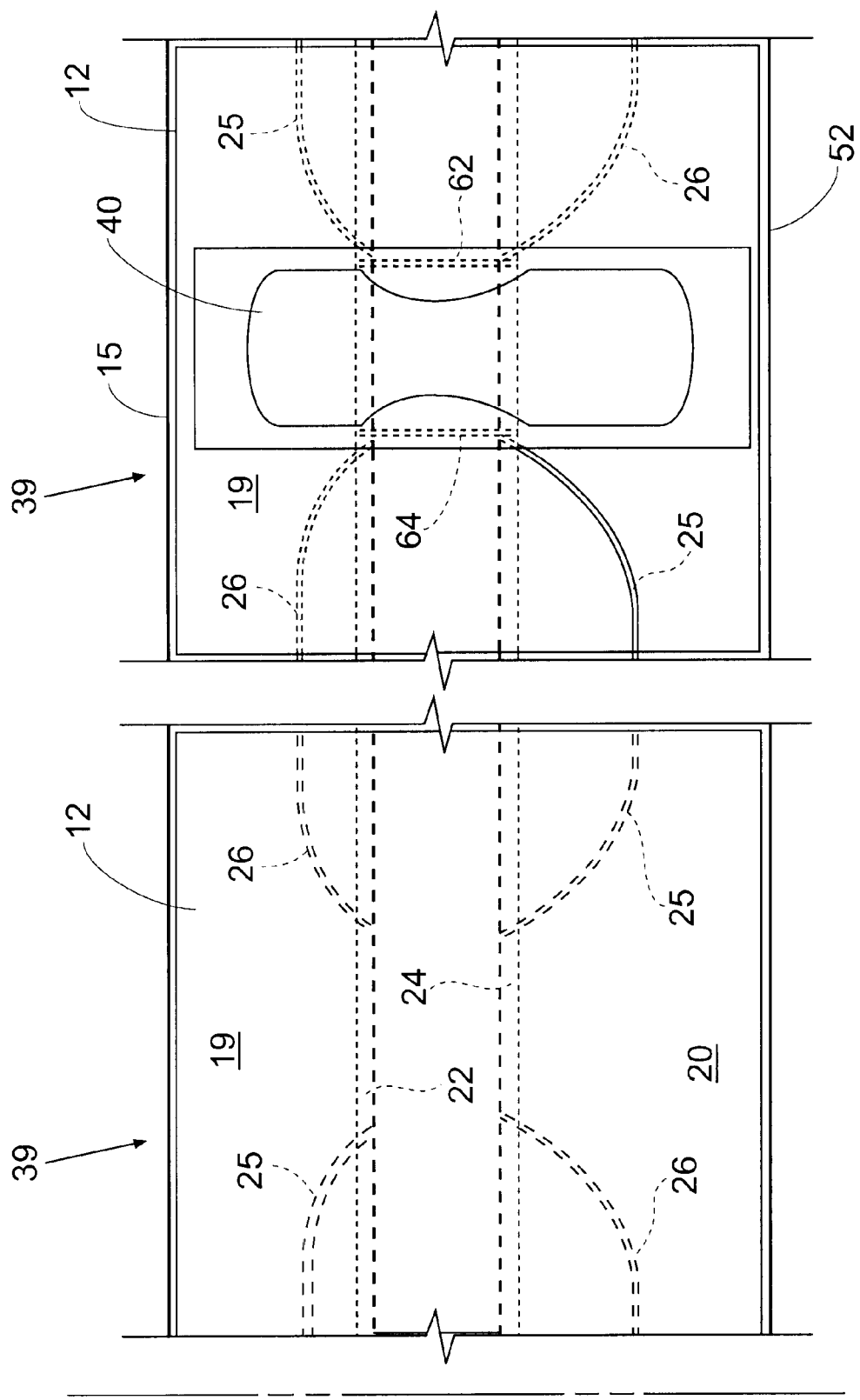

A succession of absorbent pads 40 are picked up at a supply station 41 by vacuum heads 44 of a pad supplying/turning device 42. The absorbent pads 40 are comprised of various absorbent materials contained within a non-woven cover stock which are well known in the art. The pads are rotated 90° and applied, successively, to the crotch areas of the composite web 39 by a transfer roll 46 where they are attached adhesively to the inside of the web 39 which forms the garment chassis. FIG. 5h shows a pad 40 attached to the composite web 39. It should be noted that in FIG. 5h the web 39 is being viewed from the opposite side from that which is shown in FIGS. 5a through 5g.

Leg hole materials 48, if not previously removed, are cut at a cutting station 47, thereby removing the material 48 contained within an approximate perimeter defined by the curved pattern of the elastics 25, 26. The running composite chassis web 39 is folded, before or after cutting out of the leg holes, longitudinally along its centerline, thereby aligning its front waist edge 51 with its back waist edge 52. The regions 53 which are to become the side seams 54 of the garments 50 are then welded by a sealing device 49 either ultrasonically or by heat. Note that the leg-holes are preferably cut out before this point, leaving only a narrow zone for welding. The weld pattern is preferably wide enough to extend into both the left side seam of one garment and the right side seam of the adjacent garment. The garments 50 are then separated by passing through a cut-off knife assembly 55, which severs the web along the transverse axis of the side seam weld 53.

Figure 3B:
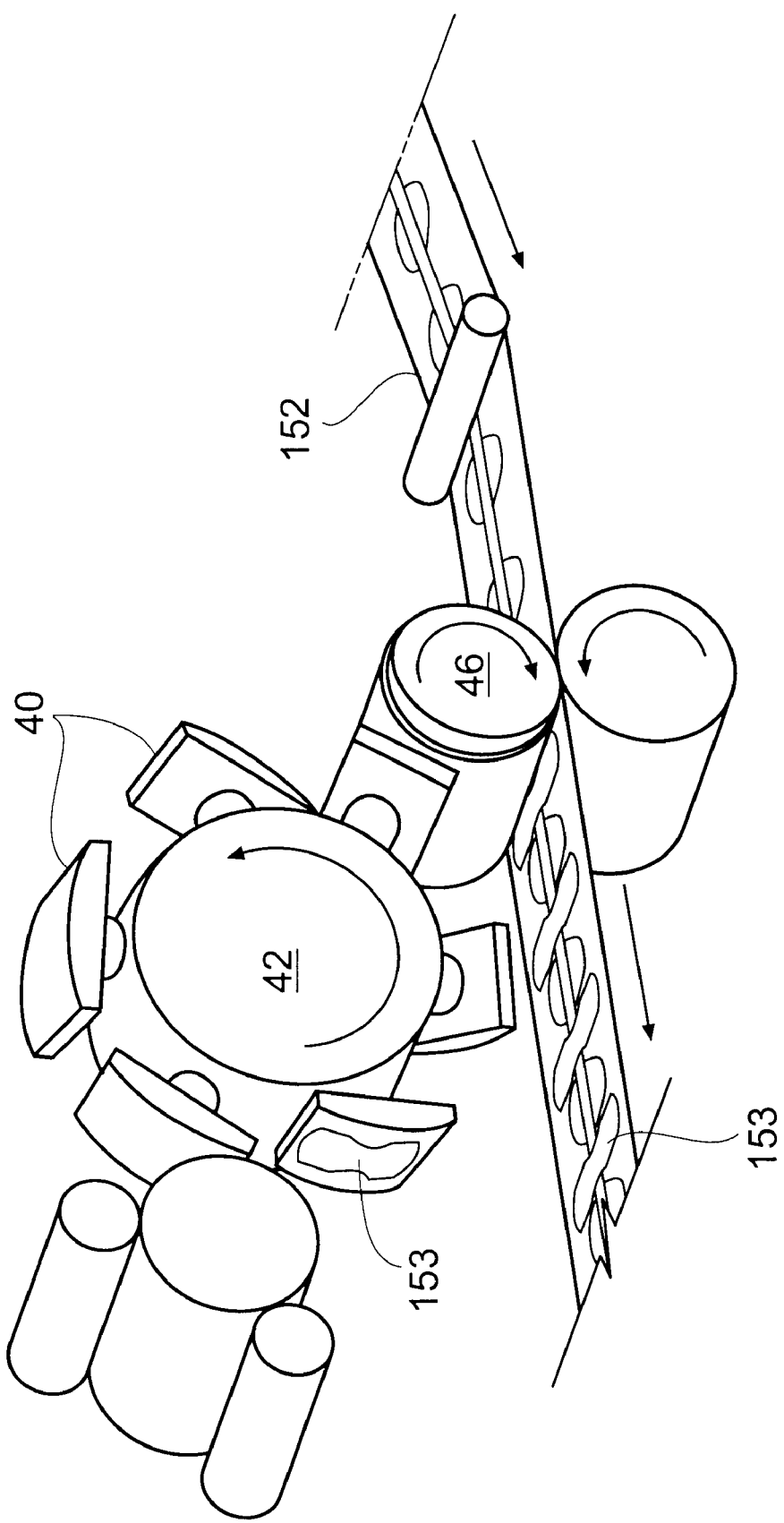

Referring to FIG. 3, there is shown an alternate embodiment of the invention which provides a process that results in bringing of the front and back leg hole elastics into closer proximity with each other. In the embodiment shown in FIGS. 3a and 3b, this is accomplished by beginning with a web of material 111 and slitting the same, for example, by means of a rotary knife 114 into two halves, 119 and 120. It will be appreciated that instead of cutting the web 111 into halves that the process could also be practiced by providing the narrower webs 119 and 120 from two separate sources of material. As shown, the two webs 119 and 120 are brought into the process utilizing two separate combining drums, 121 and 122, each of which lays down its respective web 119 and 120 onto a larger rotating drum 124. In the illustrated embodiment a narrow strip 126 is removed by means of a rotary knife 125 from web 119. Similarly a rotary knife 128 removes a strip 129 from web 120. As shown in FIG. 3a, elastic strands 130 are applied in an oscillating pattern onto web 119 at combining drum 121 and the inwardly facing edges thereof are covered by the narrow web 126. Similarly an elastic 132 is applied to web 120 immediately prior to covering of the inwardly facing edge thereof by means of narrow web 129. Adhesive patterns are applied by applicators 134 and 136, respectively, to form spray patterns 140 and 138 which are shown in FIGS. 6a and 6b. After the elastic 130 has been laid upon web 119 on combining drum 121, the inwardly facing edge thereof is cut by means of a rotary cutter 142, thereby removing a strip of scrap material 144 which includes the inner edges of web 119 and narrow strip 126 together with that portion of elastic 130 which is sandwiched therebetween. The identical process takes place on combining drum 122 with respect to web half 120 where, after lamination of elastic 132 between the inner edge of web 120 and narrow strip 129, a rotary knife 146 removes the severed portion of the webs and elastic 148. The resultant laminated webs 119 and 120 are then applied to a backsheet web 150 on combining drum 124. This results in a combined web 152, also illustrated in FIG. 6a.

Then, as in the case of the earlier described embodiment, a pad turning and supplying assembly 42 utilizing vacuum heads 40 supplies a series of absorbent pads 153 to a transfer roll 46 which applies each pad successively in each crotch area on the combined web 152. As best seen in FIG. 6b, the absorbent pads 153 may be supported on a sheet of absorbent web material 154 which is bonded to the composite web 152 by means of ultrasonic welding, heat, or, if desired, by means of adhesives. As best seen in FIG. 6a the bringing of the webs 119 and 120 into close proximity to each other makes it possible for the elastics 130 and 132 to effectively encircle the leg areas with only an insignificant gap between them. This reduces or eliminates the need for introducing elastics along the lateral edges of the pads 153.

The embodiment of FIGS. 3a and 3b is shown in diagrammatic form in FIG. 4. FIG. 4 also illustrates the steps of folding the composite web in half at a folding station 156, cutting out the leg hole material 159 and a cutting station 158. Then, side seams 161 are formed at a sealing station 160. The side seams 161 are severed along their approximate center line at another cutting station 162. This results in the finished diaper garment 164 which have side seams 161 on each side of the garment.

Figures 7D, 7E, 7F:
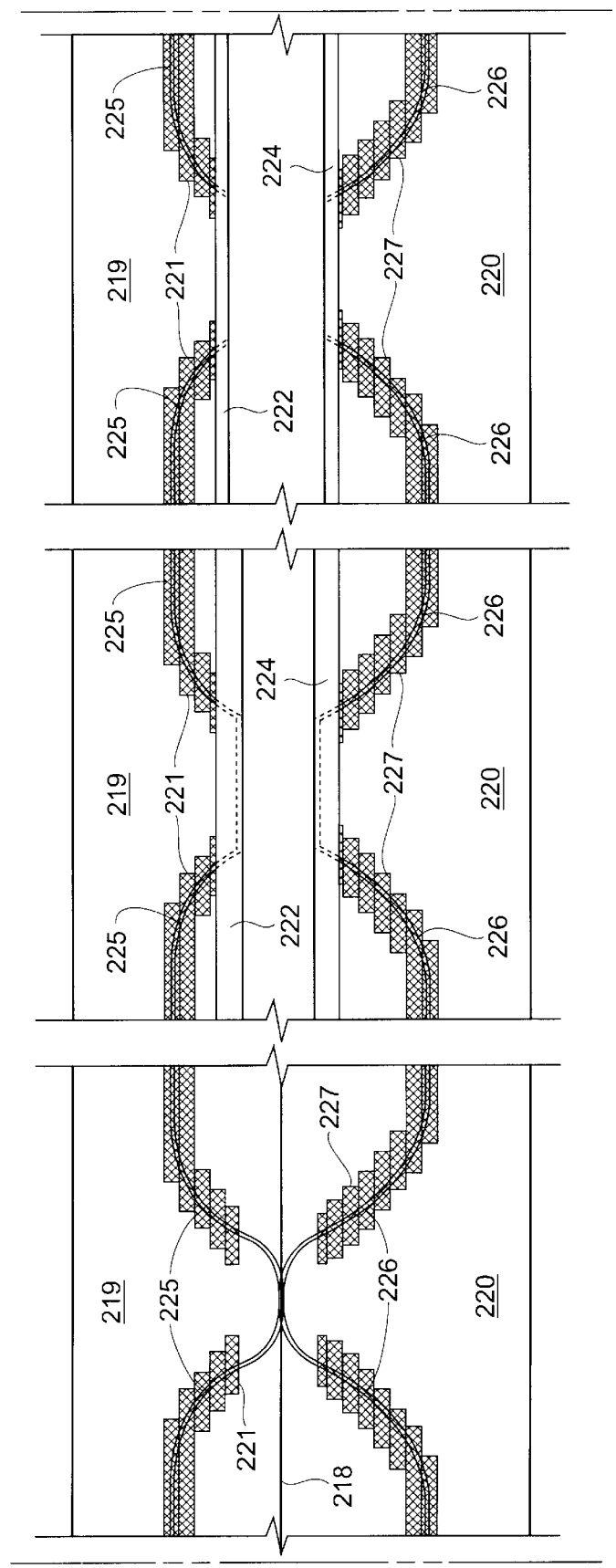
Figures 7G, 7H:
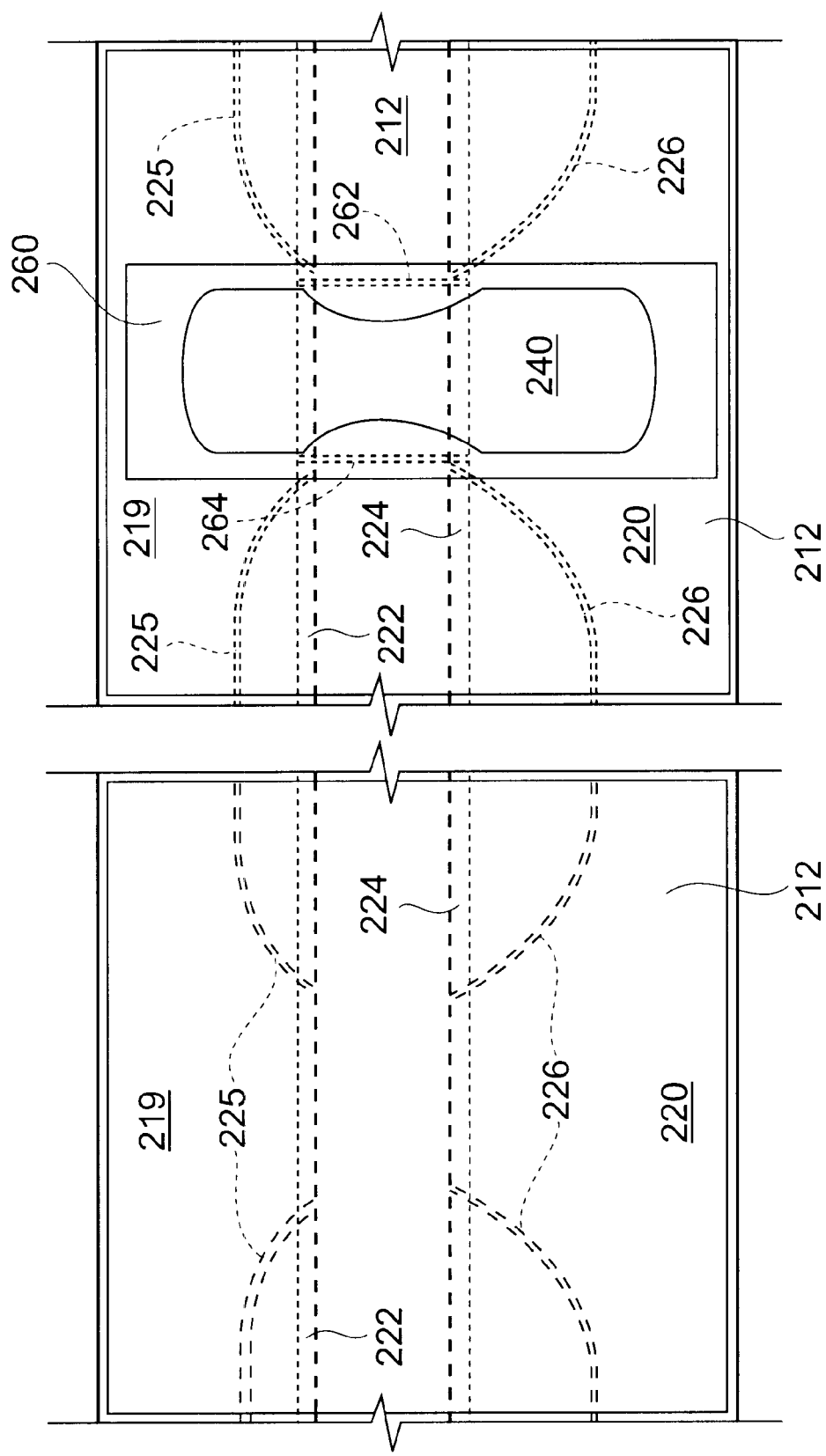
Figure 8:
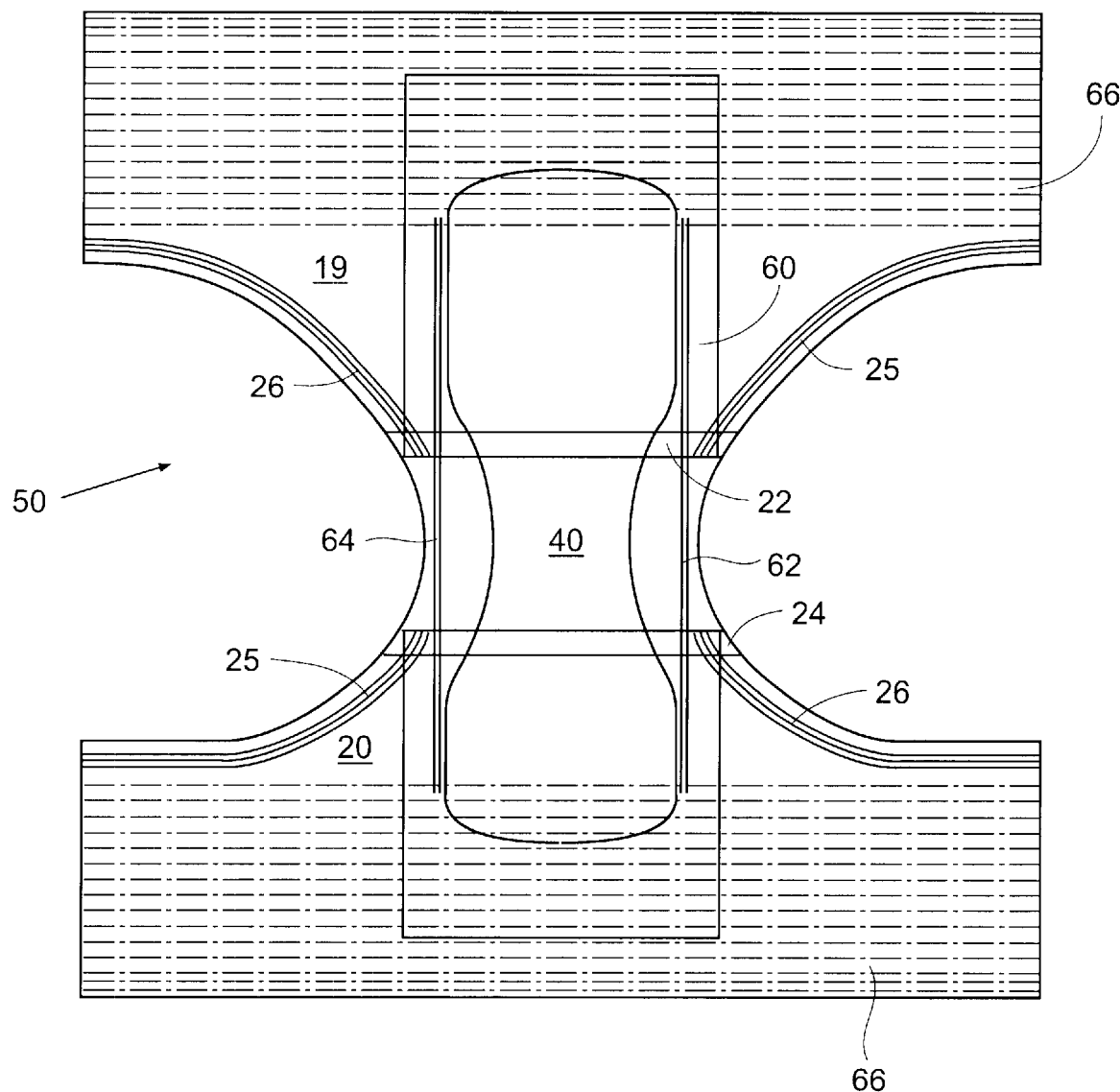
FIG. 8 is a top plan view showing an unfolded diaper blank produced in accordance with the invention with the leg openings removed.
Figure 9A:
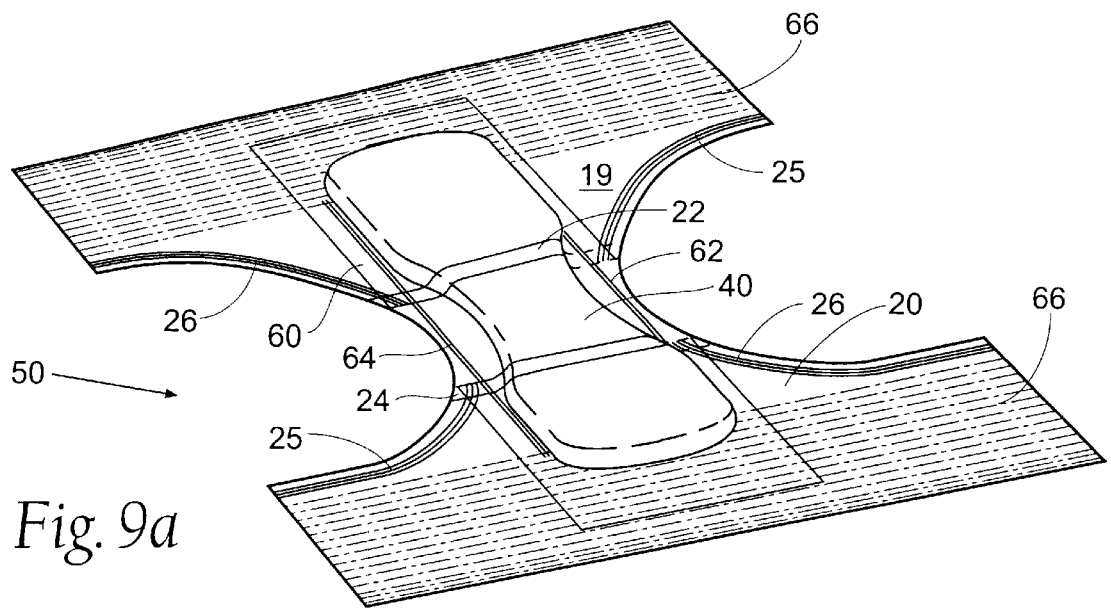
FIG. 9a is a perspective view of the diaper blank of FIG. 8.
Figure 9B:
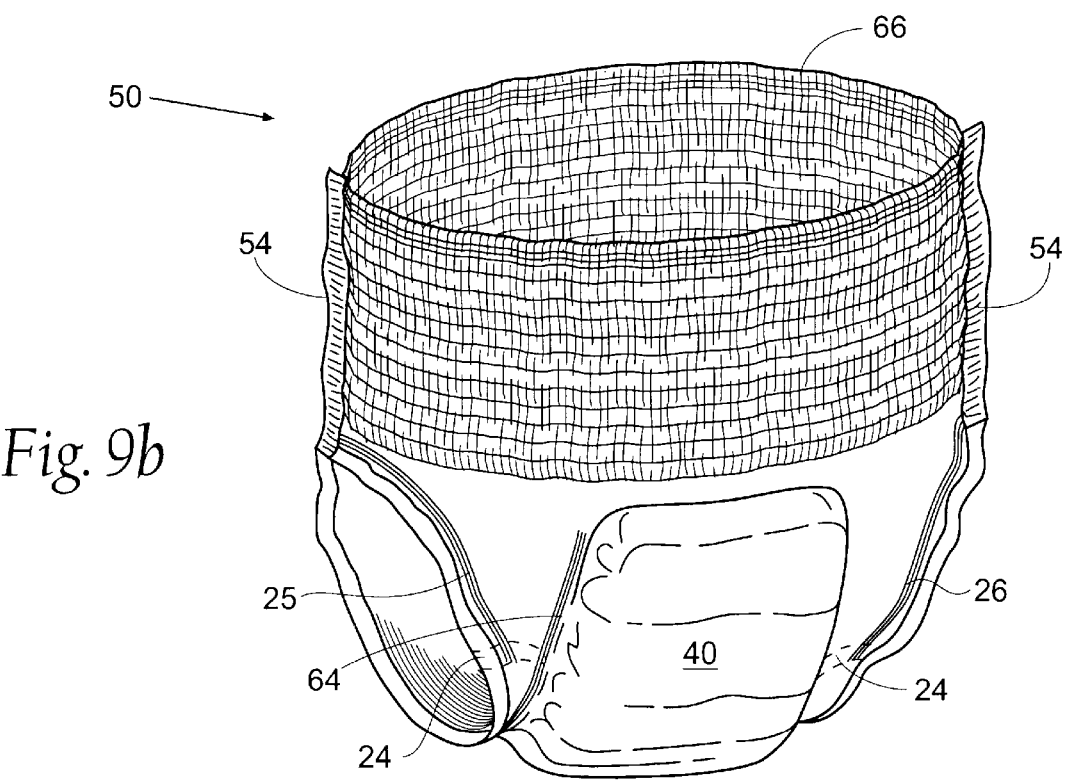
FIG. 9b is a perspective view showing the diaper of FIGS. 8 and 9a after final assembly thereof.
Figure 10:
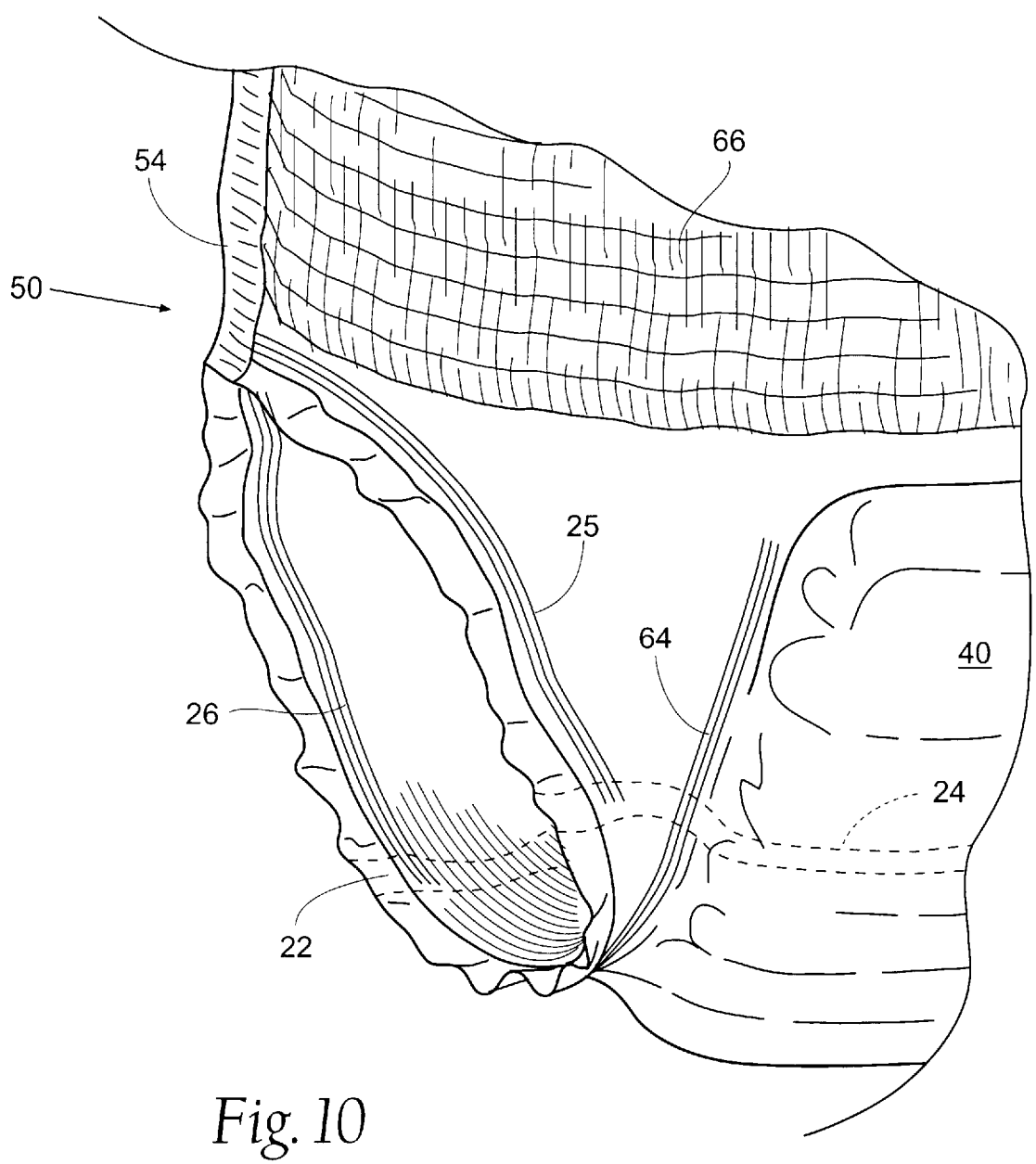
FIG. 10 is a fragmentary enlarged perspective view showing the leg opening and elastics of the diaper of FIG. 9b.

Referring to FIGS. 8–10, there is seen, in FIGS. 8 and 9a, a blank for a diaper garment 50 which may be produced by the apparatus and method shown in FIGS. 1–1c or, alternatively, by that shown in FIGS. 7a–7h. In this embodiment the leg openings have been cut out leaving the strands 25 and 26 partially encircling the leg openings. A pad 40 supported on a web 60, which may also be formed of non-woven absorbent material has been applied to the crotch area. A separate strand of elastic material 62 and 64 positioned on opposite sides of the pad 40 provides a means to complete the approximate encirclement of the leg openings by means of elastic material which, as in the earlier described embodiment, is somewhat discontinuous. Thus, the ends of elastic strands 25 and 26 which are inwardly terminating in the crotch area are secured by the narrow webs 22 and 24 as seen in FIGS. 9a and 9b, as well as in FIG. 10. The elastic strands 62 and 64 are thus spaced away from the ends of elastics 25 and 26. This arrangement provides for a comfortable fit around the legs of a wearer but without any bunching tendency in the crotch area which might cause discomfort.

Also, as seen in FIGS. 9–10 waist elastics 66 are provided on opposite sides of the garment blank which, after folding together and formation of the side seams 54, entirely encircle the waist area of the finished garment 50. Note, also, in FIGS. 9b and 10 that the ends of the elastics 25 and 26 which extend furthest away from the crotch area also become secured by means of the side seams 54.

Referring next to FIGS. 7a–7h, there is illustrated a sequence of steps illustrating yet another embodiment of the invention. In accordance with the embodiment of 7a–7h, a web 211, as depicted in FIG. 7a, is slit into two halves 219 and 220 as it travels through the process. Then, adhesive patterns 221 and 227 are applied as shown in FIG. 7c, to the respective web halves 219 and 220. Elastic strips 225 and 226 are then applied in an undulating pattern, as shown in FIG. 7d. Then, the inner edges of the webs 219 and 220 are folded over on themselves thereby covering and securing the portions of elastic strips 225 and 226 which are nearest the cut line 218 between webs 219 and 220. As also seen, the portions of elastic strands 225 and 226 which traverse the crotch region of the diaper being manufactured are captured along the fold line between folded over strip 222 and the remainder of web 219 and similarly along the fold line between the folded over portion 224 and the remainder of web 220.

Referring to FIG. 7f, the two web halves 219 and 220 are seen after severance therefrom of the inner edges or folds of the folded over flap portions 222 and 224. Thus, it will be appreciated that the ends of elastic strands 225 and 226 nearest the crotch region of the diaper are anchored in place by the remaining width of the strips 222 and 224 and the webs 219 and 220, respectively.

In FIG. 7g a cover sheet 212 has been laminated over the web halves 219 and 220. The adhesive areas 221 and 227 which flow into the webs 219 and 220 are not own in this view, since they are no longer discrete entities. The elastic strands 225 and 226 have been at this point sandwiched between the layers 212 and 219 or 220, respectively with the ends thereof firmly anchored by the narrow strips 222 and 224 which are also sandwiched between the covering web 212 and the original web halves 219 and 220.

Referring to FIG. 7h, the assembled diaper forming materials of FIG. 7g are shown from the opposite side of the web and with an absorbent pad 240 secured thereto. As in the earlier embodiments, pad 240 is attached to a supporting web 260. Also, in this case elastic strands 262 and 264 are attached to the carrier web 260 so that the gaps between the ends of each of the elastics 225 and 226 which lie closest to the diaper crotch area are provided with an elastic material. Note, again, that the strands 262 and 264 are displaced slightly from the ends of the strands 225 and 226 which are anchored by the narrow strips 222 and 224. It will, thus, be appreciated that after the removal of the leg opening materials from the combined webs of FIG. 7h, a blank is provided which is virtually identical to that shown in FIGS. 8 and 9a. Accordingly, the resultant diaper is also virtually identical to that illustrated in FIGS. 9b and 10.

Figure 11:
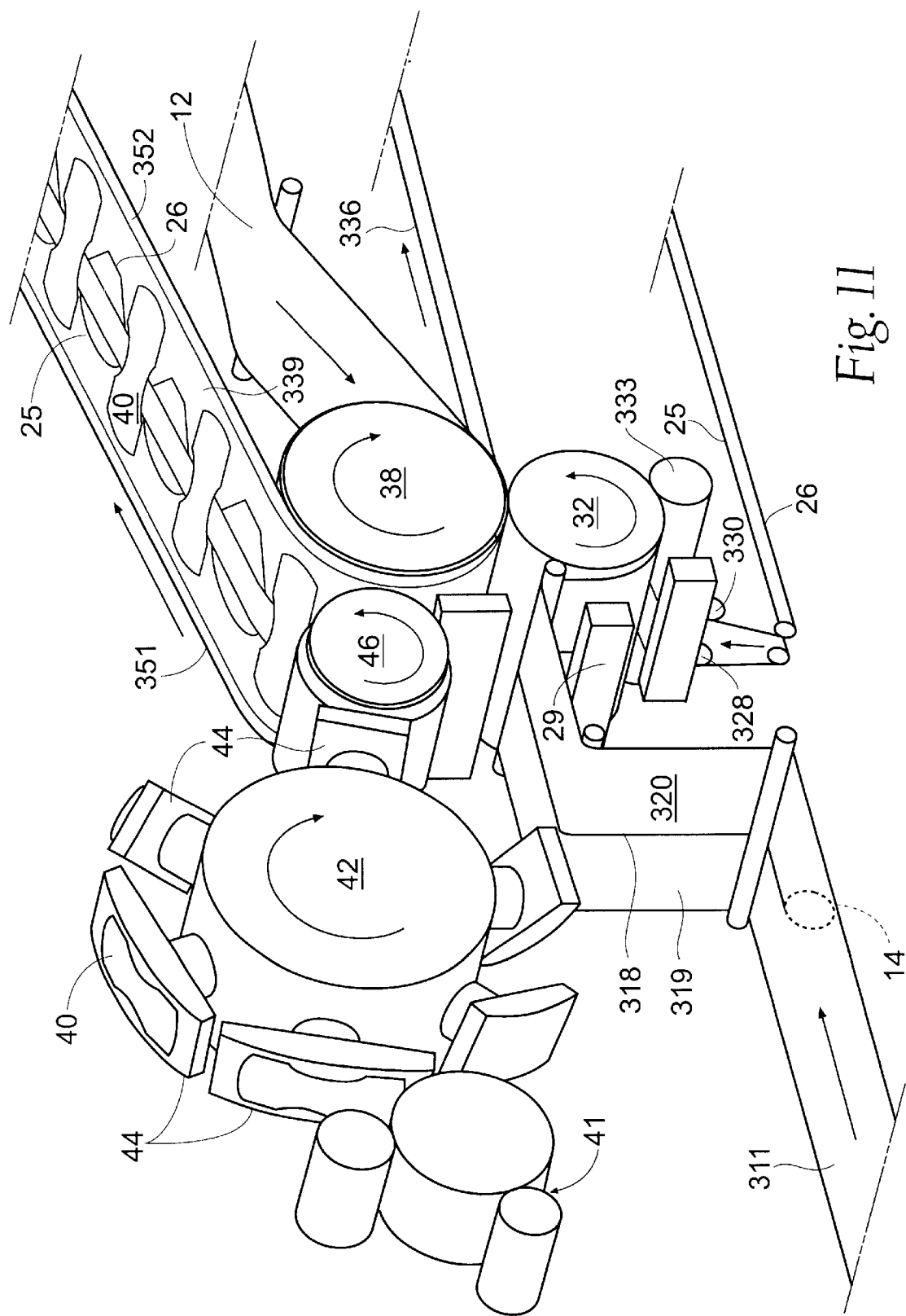
FIG. 11 is a fragmentary perspective view showing another embodiment of the invention in somewhat diagrammatic fashion.

Referring to FIG. 11, there is seen a modified process of this invention wherein the narrow covering strips 22 and 24, shown in connection with the earlier described embodiments, are not used. Instead, diapers and diaper blanks are produced wherein elastic strands 25 and 26 become sandwiched between a fabric web 311 and a back sheet 12. In FIG. 11 the apparatus and components having the same numbers used in connection the earlier described embodiments refer to the same components.

As seen in FIG. 11, a non-woven web 311 is cut along its center line, longitudinally, by means of a rotary knife 14 along a central cut line 318, thus forming two narrower web halves 319 and 320. A sequence of the processing steps relating to the web halves 319 and 320 are illustrated in part in FIGS. 12a–12c, steps which are omitted being similar to those shown in connection with the earlier-described embodiments. As in the case of the earlier embodiments, adhesive patterns 320 and 321 are applied to the web halves 319 and 320 by means of an adhesive applicator 29. Then, elastic strands 25 and 26 are laid down by means of reciprocating feeding devices 328 and 330, resulting in a pattern such as illustrated in FIG. 12b. Note that intended trim lines 340 and 342 are shown for illustrative purposes in FIGS. 12a and 12b by means of phantom lines. Note also from these figures that the adhesive patterns 321 and 327 are omitted from strips over the cut lines 340 and 342. This procedure facilitates slitting of the webs 319 and 320 along the trim lines 340 and 342, respectively. The slitting knives, thus, serve to cut the webs along these lines 340 and 342 without undo accumulation of adhesive on the knives.

The web halves 319 and 320 are shown subsequent to slitting and removal of the elastic strips 25 and 26 from the crotch area in FIG. 12c. It will then be appreciated that when an outside covering web 12 is applied over the parallel traveling web halves 319 and 320 that the elastic strands 325 and 326 will be sandwiched between the webs 12 and 319 or 320 and thus firmly held in place. Only a small, inconsequential end of each of the strands 25 or 26 adjacent to the slit lines 340 and 342 is left unanchored by the adhesives.

Referring to FIGS. 13a–13c in conjunction with FIG. 11, a further embodiment of the invention will be described. In this variation the web 311 is not slit by a rotary knife prior to application of the adhesive patterns thereto. Thus, the rotary knife 14 of FIG. 11 can be omitted. As seen in FIG. 13a, the web 311 is intact when the adhesive patterns 421 and 427 are applied. In other respects, these adhesive patterns are similar to those illustrated in FIGS. 12a–12c. As in that case, the trim lines 440 and 442 are again shown by means of phantom lines. Also, again, the adhesive patterns 421 and 427 can be configured so that adhesive is omitted from strips along the intended trim lines. After application of elastic strands 25 and 26 over the adhesive patterns 421 and 427, the web 311 is slit along the two parallel lines 440 and 442 resulting in two web segments 419 and 420, as seen in FIG. 13c. As noted by a comparison of FIGS. 12c and 13c, both of these procedures result in virtually identical diaper blanks. Subsequently, the leg hole areas are removed as in the case of the earlier embodiments and waistband elastics can be applied at a convenient point in the process. Then, the blanks are formed into finished diapers, just as in the case of the earlier described embodiments.

While various preferred embodiments of the invention have been shown for purposes of illustration, it will be apparent to those skilled in the art that various additional modifications can be made falling within the scope of the invention as defined by the appended claims.

We claim:

1. A disposable garment comprising a front body portion, a back body portion and an intermediate crotch portion, spaced left and right leg openings on opposite sides of said crotch portion, edges of said front and back body portions being joined to form a waist portion, said leg openings each having an upper periphery adjacent to said waist portion and a lower periphery adjacent to said crotch portion, and wherein said garment includes a back sheet which forms an outer surface thereof, a top sheet and an absorbent pad positioned in said crotch area, the improvement wherein front left and right elastic strands extend, respectively, around a quadrant of each of said leg openings from forward ends which terminate at a forward part of said crotch portion and extend around said upper periphery of each of said left and right leg openings to said side seam and rear left and right elastic strands extend, respectively, around another quadrant of each of said leg openings from rearward ends which terminate at a rearward part of said crotch portion and extend around said upper periphery of each of said left and right leg openings to said side seam, said strands being adhered to said top sheet, and to first and second narrow webs sandwiched between said top sheet and said back sheet, said first narrow web being adhered to said forward ends of each of said left and right elastic strands and said second narrow web being adhered to said rearward ends of each of said left and right elastic strands.

2. A disposable garment according to claim 1 wherein left and right elastic strands extend, respectively along the left and right edges of said absorbent pad.

3. A disposable garment according to claim 2 wherein said left elastic strands are adjacent to but do not intersect the forward ends of said front left elastic strands and the rearward ends of said rear left elastic strands and said right elastic strands are adjacent to but do not intersect the forward ends of said front right elastic strands and the rearward ends of said rear right elastic strands.

4. A disposable garment according to claim 1 wherein the ends of each of said elastic strands situated furthest from said crotch area are sealed into said side seams of said garment.

5. A disposable garment according to claim 2 wherein said left and right elastic strands which extend along the edges of said absorbent pad are adjacent to but do not intersect the ends of said front and rear left and right elastic strands.

6. A disposable garment according to claim 1 further comprising elastics encircling the waist band area of said garment.

7. (once amended) A pants-type diaper blank formed according to the method of forming blanks which are adapted to be formed into pants type diapers comprising providing first and second parallel traveling webs having inner edges facing each other, defining on said first and second webs a portion of a pants type diaper including locations thereon for leg openings and a crotch area therebetween, applying a layer of adhesive on said webs around said leg openings, laying down elastic strips on said adhesive in a semicircular pattern around said leg opening locations on both of said first and second traveling webs and through said crotch area, said elastic strips being bonded to each of said inner webs and having unbonded portions thereof between said webs, longitudinally slitting said first and second traveling webs to sever at least a portion of said webs along said inner edges and severing said elastic in said crotch area, removing said severed portion of said first and second traveling webs and said elastic, laminating a cover sheet over the remaining first and second traveling webs, and, cutting and removing all material from said leg openings.

8. A pants-type diaper produced by the method of forming pants type diapers comprising providing a traveling fabric web, defining on said web a portion of a pants type diaper including locations thereon for leg openings and a crotch area therebetween, applying an adhesive pattern on said web around said leg openings, laying down strips of elastic material on said adhesive in an undulating pattern around said leg opening locations on said traveling web and across said crotch area, forming a pair of parallel longitudinal slits along the center of said traveling web to sever said central portion of said web thereby severing said elastic in said crotch area, removing said severed portion of said traveling web and said elastic, laminating a cover sheet over the severed first and second halves of said traveling web, cutting and removing all material from said leg openings, severing said web into individual diaper blanks, folding said blanks in half across said crotch area, and, sealing the edges of said blank together on each side thereof to form a pants-type diaper.

* * * * *

UNITED STATES PATENT AND TRADEMARK OFFICE
CERTIFICATE OF CORRECTION

PATENT NO.    : 6,521,320 B2                                                                Page 1 of 1
DATED         : February 18, 2003
INVENTOR(S)   : John A. McCabe, Richard J. Nehrlich and Bradley M. Dahmer It is certified that error appears in the above-identified patent and that said Letters Patent is hereby corrected as shown below:

Title page,
Item [54], Title, delete "PRODUCTING" and substitute -- PRODUCING --

Column 10,
Line 59, delete "(once amended)".

Signed and Sealed this

Second Day of December, 2003

JAMES E. ROGAN
*Director of the United States Patent and Trademark Office*